United States Patent [19]
DeMarco

[11] Patent Number: 6,107,303
[45] Date of Patent: Aug. 22, 2000

[54] TREATMENT OF EPSTEIN BARR INFECTION

[76] Inventor: Charlene C. DeMarco, 462 S. Philadelphia Ave., Egg Harbor, N.J. 08215

[21] Appl. No.: 09/268,889

[22] Filed: Mar. 15, 1999

[51] Int. Cl.[7] .......................... A61K 31/52; A01N 43/90
[52] U.S. Cl. ........................................ 514/262; 514/264
[58] Field of Search ...................... 514/262, 264

[56] References Cited

U.S. PATENT DOCUMENTS

| | | | |
|---|---|---|---|
| 4,199,574 | 4/1980 | Schaeffer | 424/200 |
| 4,435,449 | 3/1984 | Sterm | 424/330 |
| 4,609,662 | 9/1986 | Krenitsky | 514/262 |
| 4,942,166 | 7/1990 | Harnden et al. | 514/262 |
| 4,957,924 | 9/1990 | Beauchamp | 514/262 |
| 5,061,708 | 10/1991 | Krenitsky | 514/262 |
| 5,079,252 | 1/1992 | Beauchamp | 514/262 |
| 5,164,395 | 11/1992 | Blumenkopf | 514/262 |
| 5,284,837 | 2/1994 | Lindborg et al. | 514/81 |
| 5,318,974 | 6/1994 | Beauchamp | 514/274 |
| 5,405,850 | 4/1995 | Blumenkopf | 514/262 |
| 5,543,414 | 8/1996 | Nestor et al. | 514/262 |
| 5,559,114 | 9/1996 | Exley | 514/261 |
| 5,580,571 | 12/1996 | Hostetler | 424/443 |
| 5,585,379 | 12/1996 | Sintov et al. | 514/262 |
| 5,627,185 | 5/1997 | Gosselin et al. | 514/269 |
| 5,643,891 | 7/1997 | Rideout et al. | 514/50 |
| 5,674,849 | 10/1997 | Twist et al. | 54/15 |
| 5,677,308 | 10/1997 | Lerner | 514/262 |
| 5,872,123 | 2/1999 | Lerner | 514/258 |

FOREIGN PATENT DOCUMENTS

| | | | |
|---|---|---|---|
| 84 31973 | 8/1984 | Australia | C07D 473/18 |
| 0141927 A2 | 10/1984 | European Pat. Off. | C07D 473/18 |

OTHER PUBLICATIONS

Harnden et al M.R., Prodrugs of the Selective Antiherpes Agent 9–[4–Hydroxy–3–(hydroxymethyl)but–1–yl] guanine (BRL 39123) with Improved Gastrointestinal Absorption Properties, *J. Med. Chem.*, vol. 32, 1738 (1989).

Abstract No. 106:113183n, Van der Horst, C., et al., Differential effect on acyclovir and 9–(1, 3–dihydroxy–2–propoxymethyl) guanine on herpes simplex virus and Epstein–Barr virus in a dually infected human lymphoblastoid cell line, *Chemical Abstracts—Pharmacology*, vol. 106, p. 21 (1987).

Abstract No. 106:168524e, Faerber, I., et al., Effect of (E)–5–(2–bromovinyl) and 5–vinyl–B–(D)–arabinofuranosyluracil on Epstein–Barr virus antigen expression in P3HR–1 cells: comparison with acyclovir, *Chemical Abstracts*, vol. 106, p. 22 (1987).

Abstract No. 125:157838b, Tynell, E., et al., Acyclovir and prednisolone treatment of acute infectious mononucleosis: A multicenter, double–blind, placebo controlled study, *Chemical Abstracts—Pharmacology*, vol. 125, p. 43 (1996).

Abstract No. 122:204641g, Ertl, P., et al., A comparative study of the in vitro and in vivo antiviral of acyclovir and penciclovir, *Chemical Abstracts—Pharmacology*, vol. 122, p. 36 (1995).

Abstract No. 120:260453t, Hughes, P., et al., Effect of acylation on the ocular disposition of acyclovir.I: Synthesis, physiochemical properties, and antiviral activity of 2'–esters, *Chemical Abstracts—Pharmacology*, vol. 120, p. 15 (1994).

Abstract No. 109:121992c, Lin, J.C., et al., Comparison of two bromovinyl nucleoside analogs, 1–B–D–arabinofuranosyl–E–5–(2–bromovinyl) uracil and E–5–(2–bromovinyl)–2'–deoxyuridine, with acyclovir in inhibition of Epstein–Barr virus replication, *Chemical Abstracts*, vol. 109, p. 14 (1988).

Abstract No. 123:47449b, Bacon, T., et al., Activity of peniclovir against Epstein–Barr virus, *Chemical Abstracts*, vol. 123, p. 30 (1995).

Abstract No. 126:165990f, Webster, A., et al., Developments in anti–herpes virus therapy, *Chemical Abstracts—Pharmacology*, vol. 126, p. 4 (1997).

Abstract No. 126:194733e, Acosta, E., et al., Valacyclovir, *Chemical Abstracts—Pharmacology*, vol. 126, p. 6 (1997).

Abstract No. 126:210p, Perry, C., et al., Valaciclovir: A review of its antiviral activity, pharmacokinetic properties and therapeutic efficacy in herpesivirus infections, *Chemical Abstracts—Pharmacology*, vol. 126, p. 16 (1997).

Perry et al, 126CA:210, 1996.
Crooks et al, 121CA:194728, 1994.
Ertl et al, 122CA:204641, 1995.
Datta et al, 94CA:10887, 1980.

*Primary Examiner*—Russell Travers

[57] ABSTRACT

A method of treating Epstein Barr virus infection in humans by administering a pharmaceutically effective amount of an antiviral agent selected from a group consisting of acyclovir, famciclovir, valacyclovir and a pharmaceutically acceptable salt thereof is provided.

4 Claims, No Drawings

TREATMENT OF EPSTEIN BARR INFECTION

BACKGROUND OF THE INVENTION

Epstein Barr Virus (EBV) is a herpesvirus that infects 95% of the population world wide. EBV is the causative agent for infectious mononucleosis and is also closely associated with nasopharyngeal carcinoma, Burkitt's Lymphoma in Africa and the growth of smooth-muscle tumors after organ transplants. The symptoms of the EBV invention includes fatigue, low grade fever, lymphadenopathy and sore throat. Some patients experience a more severe infection with splenomegaly. EBV takes a fulminant course in patients infected with HIV. In EBV infections, once the initial episode resolves, the virus becomes latent and can be reactivated later in life. A few EBV infections remain chronically active.

To date, no effective treatment for EBV exists. Accordingly, a need for such a treatment is evident.

SUMMARY OF THE INVENTION

This invention is directed to a method of treating mammals, including humans, infected with Epstein-Barr virus by administering to a mammal in need thereof of a pharmaceutically effective amount of acyclovir, famciclovir, valacyclovir or a pharmaceutically acceptable salt thereof.

It has unexpectedly been discovered that antiviral agents acyclovir, famciclovir, and valacyclovir and a pharmaceutically acceptable salt thereof, are useful in treating mammals, including humans, infected with EBV.

DETAILED DESCRIPTION OF THE INVENTION

Antiviral agents of the present invention include acyclovir, famciclovir, valacyclovir and a pharmaceutically acceptable salt thereof. Acyclovir, famciclovir and valacyclovir have known uses for treating herpesvirus zoster (shingles) and genital herpes. Acyclovir is also indicated for treatment of chickenpox.

U.S. Pat. No. 4,199,574, incorporated herein by reference, describes the preparation of acyclovir, also known as 2-amino-1,9-dihydro-9-[(2-hydroxyethoxy)methyl]-6H-purin-6-one. Acyclovir is currently marketed under the trademark Zovirax.

Valacyclovir is a generic name for L-valine 2-[(2-amino-1,6-dihydro-6-oxo-9H purin-9-yl)methoxy]ethyl ester. It is the L-valine ester of acyclovir and its preparation is described in U.S. Pat. No. 4,957,924, which is incorporated herein by reference. Valacyclovir is currently marketed under the trademark Valtrex.

Famciclovir is a generic name for 2-[2-(2-amino-9H-purin-9-yl)ethyl]-1,3-propanediol diacetate. It's preparation is described in Australian patent application No. 84 31,973 and M. R. Hamden et al., *J.Med.Chem.*, vol. 32, 1738 (1989), which are incorporated herein by reference. Famciclovir is currently marketed in the United States under the trademark Famvir.

As defined herein, a "therapeutically effective" amount of acyclovir, valacyclovir, famciclovir or a pharmaceutically acceptable salt thereof is a non-toxic amount which alleviates the symptoms associated with EBV infection.

Furthermore, as defined herein, the phrase "method of treating" is not limited to elimination of the symptoms or elimination of the virus, but also refers to alleviation of the symptoms associated with EBV infection or deactivation of the virus. Epstein Barr virus is easily reactivated after primary infection. Many factors can contribute to reactivation of the latent Epstein Barr virus including, but not limited to, malnourishment, overwork, lack of sleep or concurrent disease. Anything that stresses the immune system allows the virus to become active. Recurrences are similar to those seen with other herpesviruses. Acyclovir, valacyclovir and famciclovir are useful in deactivating the virus. While use of these anti-viral agents can suppress EBV effectively and provide significant symptomatic relief, it is not clear whether the virus is permanently eliminated. Thus, retreatment may be necessary in some individuals.

EBV infections are associated with several known diseases. Examples include, but are not limited to, mononucleosis, chronic fatigue syndrome, nasopharyngeal carcinoma, Burkitt's Lymphoma and the growth of smooth-muscle tumors after organ transplants.

The antiviral agent of the present invention may be administered by any suitable route including oral, rectal, nasal, topical, vaginal, parenteral. Preferred mode of administration is oral.

The antiviral agent of the present invention may be formulated into tablets, capsules or other oral dosage forms containing one or more pharmaceutically acceptable carriers, such as lactose, cornstarch, hydroxypropylmethylcellulose, microcrystalline cellulose as well as other excipients known in the art.

In addition to the aforementioned ingredients, the pharmaceutical composition of this invention may include one or more of additional ingredients, e.g., pharmaceutically acceptable carriers such as diluents, buffers, flavoring agents, binders, surface active agents, thickeners, lubricants, preservatives and the like.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

The amount of the antiviral agents required to constitute a "therapeutically effective amount" will vary based on a number of factors, including the severity of the symptoms and the identify and chemical makeup of the patient, and a mode of administration. In the case of oral administration, the preferred dosages are as follows: for valacyclovir, 500 mg once or twice daily for two to sixteen weeks; for famciclovir, 125 mg or 250 mg, once or twice daily, for two to sixteen weeks; and for acyclovir, 200 mg once or twice daily for two to sixteen weeks.

For example, valacyclovir may be administered orally to patients in doses ranging from 500 mg once daily to 1000 mg three times per day. The dosage is dependent on the patient's weight and the extent of disease. It should be modified if renal disease is present and would reflect the level of creatinine clearance. For example, the creatinine clearance was greater than or equal to 50 ml/min, the dose preferably should not exceed 500 mg twice a day. If the creatinine clearance was between 30–49 ml/min, the dose preferably should not exceed 500 mg once a day. Mild hepatic disease does not preclude treatment with this drug. Valacyclovir should be used with supervision in patients with advanced HIV infection and in bone marrow or renal transplant patients. Pregnant females, nursing mothers or pediatric patients should not receive valacyclovir unless the risk of infection outweighs its use. The most preferred dosage is 500 mg twice a day. Preferable duration of administration is between two and sixteen weeks.

In an embodiment of the present invention, famciclovir may be given orally in doses ranging from 125 mg once daily to 5 mg three times a day. It is well understood in the art that in cases of renal impairment, the dosage should be adjusted accordingly. For instance, if a creatinine clearance is between 40–59 ml/min, the recommended maximum dose is 250 mg twice daily. If a creatinine clearance is between 20–39 ml/min, the recommended maximum dose is 250 mg once daily or 125 mg twice daily. Mild hepatic disease does not preclude treatment with famciclovir. Famciclovir is not recommended for use in pregnant women or children. Preferred duration of therapy is eight weeks. Preferred dose is 250 mg twice daily.

In another embodiment of the present invention, acyclovir may be given orally in doses from 200 mg once daily to 400 mg four times daily. Preferably, the dose should not exceed 400 mg twice daily in patients with compromised renal function. Children may be treated with acyclovir at 20 mg per kg four times per day. Children weighing more than forty kg may be dosed as an adult. Children weighing less than forty kg are rarely infected with EBV unless unusual circumstances prevail. Treatment for initial EBV infection may be 200 mg four times per day for ten days. For reactivated EBV infection in an adult, preferred dosage is 400 mg twice a day for four weeks.

The following example section describes embodiments of the present invention and should not be construed as limiting.

EXAMPLE I

Patients infected with Epstein Barr virus were treated with the antiviral agents of the present invention: acyclovir, valacyclovir and famciclovir. To confirm infection, serology was done prior to treatment using a western blot for EBV. In addition, a complete blood count to access immune system function and hematological status and chemistry analysis to check liver and kidney function prior to therapy were performed. The latter tests were repeated during and after treatment to determine the existence of adverse phenomena as a result of treatment. The EBV western blot was also repeated after therapy was completed to demonstrate efficacy. All patients displayed symptoms consistent with EBV infection, most notably fatigue.

The test group consisted of 29 patients, 18 of whom were female and 11 were male. Their ages ranged from 16 to 56. All complained of fatigue as the main symptom. 11 percent of these patients showed serological evidence of initial infection with EBV virus. The remainder were divided into 16 percent chronic infection and 72 percent reactivated EBV infection. Of the 29 patients, 3 were treated successfully with famciclovir, 25 with valacyclovir only and one with acyclovir. No patients were given a placebo.

After initial testing, patients were treated for four week intervals. Treatment ranged from administration of 500 mg valacyclovir once daily for two weeks to twice daily for 16 weeks; famciclovir from two to 16 weeks, including administration of 125 mg twice a day for 16 weeks and 250 mg once a for 8 weeks; acyclovir 200 mg a day for 8 weeks (please verify the dosage and frequency of administration information).

The patients were seen every four weeks for assessment of symptoms and to obtain serological data. The goal of therapy was resolution of symptoms. At monthly appointments, only five patients reported adverse effects; one with mild headache, two noted mild nausea and headache, and one with nausea alone. This occurred in the initial four weeks of therapy and resolved spontaneously or responded to a change in dose or medication. One patient experienced disorientation and light-headedness while taking valacyclovir but did not experience any side effects using acyclovir. It is not certain if these abnormalities were due to treatment with valacyclovir or not. No one stopped medication because of adverse effects. Repeat lab testing did not show any incidence of hepatic, renal, immune or hematological dysfinction related to use of this group of pharmaceuticals. A summary of these treatments is provided below in a table format. In this table, day 1 refers to the day the treatment began; "bid" stands for "twice a day"; and "od" stands for "once a day."

| PATIENT | MEDICATION | ADVERSE REACTION | RESPONSE | EBV WESTERN BLOT |
|---|---|---|---|---|
| 1 | Valacyclovir 500 mg od for 12 wks | None | Fatigue resolved; sore throat better as of 1/28/98; no recurring symptoms | Positive on Day 1; negative approx. 2, 5 and 7 mos from Day 1 |
| 2 | Valacyclovir 500 mg bid for 8 wks | None | Fatigue, sore throat and swollen glands resolved; will go back on Valacyclovir 500 mg bid for 4–8 wks | Positive on Day 1; negative approx. 5 mos from Day 1; positive approx. 9 mos. after Day 1 (symptoms returned) |
| 3 | Valacyclovir 500 mg od for 4 wks; Valacyclovir 500 mg bid for 4 wks; Famciclovir 125 mg bid for 16 wks | None | Fatigue finally improved | Positive on Day 1 and approx. 2 and 4 mos from Day 1; negative approx. 8 mos from Day 1 |
| 4 | Valacyclovir 500 mg od for 12 wks; Famciclovir 250 mg od for 8 wks | None | Fatigue improved | Positive on Day 1; negative approx. 5 mos. from Day 1 |

-continued

| PATIENT | MEDICATION | ADVERSE REACTION | RESPONSE | EBV WESTERN BLOT |
|---|---|---|---|---|
| 5 | Valacyclovir 500 mg od - BID intermittently over 1 yr; 4–8 wks at a time | None | Symptoms improve then reoccur; minor changes in test results; Valacyclovir allows patient to resume work and function; chronic infection | Positive on Day 1; positive approx. 4 mos. and 8 mos from Day 1 |
| 6 | Valacyclovir 500 mg od for 4 wks, then Valacyclovir 500 mg bid for 8 wks | None | Significant improvement after increasing dose to bid - fatigue vastly improved, even exercising | Positive on Day 1; negative approx. 4 mos. from Day 1 |
| 7 | Valacyclovir 500 mg od for 4 wks; Valacyclovir 500 mg bid for 12 wks; Valacyclovir 500 mg tid for 12 wks | None | Significant improvement; initially patient unable to work - now working full time and caring for family; minimal lab changes | Positive on Day 1 and approx. 4 and 7 mos. from Day 1 |
| 8 | Valacyclovir 500 od for 16 week; Valacyclovir 500 bid for 2 weeks | None | EBV panel -; major decrease in symptoms; no benefit from inc to bid; weaned off | |
| 9 | Valacyclovir 500 od to bid for 4–6 weeks | None | Transient relief of symptoms with reoccurences; chronic, remitting with meds, EBV. | |
| 10 | Valacyclovir 500 od for 8 weeks | Slight nausea initially - resolved in one week | Fatigue gone; decreased antibody | |
| 11 | Valacyclovir 500 bid for 8 weeks | None | Fatigue, sore throat gone; EBV ab down | |
| 12 | Valacyclovir 500 for 4 weeks - famiclovir 250 mg od | None | Valacyclovir lessened fatigue slightly. Famiclovir improved energy and sore throat | |
| 13 | Valacyclovir 500 od for 4 weeks; Valacyclovir 500 bid for 12 weeks; Valacyclovir 500 od for 4 weeks | None | Significant improvement - fatigue, sore throat. Lasts for several months and reoccurs. | |
| 14 | Valacyclovir 500 od for 1.5 weeks - felt nauseous and HA - switched to acyclovir 200 od for 8 weeks - tolerated this well. | Headache and nausea with Valacyclovir - pt stopped 2.5 weeks later started acyclovir 200 od without problem | Fatigue and sore throat and swollen glands much improved - EBV ab level unchanged. Symptomatic | |
| 15 | Valacyclovir 500 bid for 8 weeks | None | Fatigue, sore throat and swollen glands gone | |
| 16 | Valacyclovir 500 bid for 8 weeks | None | Fatigue significantly improved; EBV ab decreased | |
| 17 | Valacyclovir 500 od for 4 weeks | | | |
| 18 | Valacyclovir 500 mg od for 4 wks | — | | Positive on Day 1; positive approx. 10 mos from Day 1 |
| 19 | Valacyclovir 500 mg od for 4 wks, 2 wk intervals | Headache if taken longer than 2 wks; no headache if taken for 2 wks; off for 2 wks; then repeat 2 wks of Valacyclovir | Fatigue significantly reduced; decreased EBV antibodies | Positive on Day 1; negative approx. 2 mos from Day 1 |
| 20 | Valacyclovir 500 mg bid for 4 wks | None | Fatigue significantly improved | Positive on Day 1; no retest |
| 21 | Valacyclovir 500 mg bid for 4 wks; Valacyclovir 500 mg od for 4 wks | None | Fatigue improved - patient able to exercise - EBV; intermittently active infection - suppressed each time with Valacyclovir | Positive on Day 1; negative approx. 2 mos from Day 1 |

-continued

| PATIENT | MEDICATION | ADVERSE REACTION | RESPONSE | EBV WESTERN BLOT |
|---|---|---|---|---|
| 22 | Valacyclovir 500 mg od for 16 wks | None | Resolution of fatigue and sore throat; EBV | Positive on Day 1; negative approx. 4 mos from Day 1 |
| 23 | Valacyclovir 500 mg od for 12 wks; Valacyclovir 500 mg bid for 8 wks | None | Resolution of fatigue, sore throat and swollen glands; EBV | Positive on Day 1; negative approx. 6 mos from Day 1 |
| 24 | Valacyclovir 500 mg bid for 8 wks | None | Fatigue and sore throats significantly reduced; EBV titer negative - not done for 1 yr but symptoms gone within 8 wks | Positive on Day 1; negative approx. 14 mos from Day 1 |
| 25 | Valacyclovir 500 mg od for 2 wks; then Valacyclovir od every other day for 3 wks | None at this rate; if higher headache and nausea | Fatigue gone; EBV titer negative | Positive on Day 1; negative approx. 5 mos from Day 1 |
| 26 | Valacyclovir 500 mg od for 2 wks | None | Fatigue improved after first 2 wk interval | Positive on Day 1; no retest |
| 27 | Valacyclovir 500 mg bid for 12 wks | None | Fatigue, sore throat and swollen glands gone; EBV negative | Positive on Day 1; negative 6 mos from Day 1 |
| 28 | Famciclovir 250 for 8 weeks bid | None | Clinically improved; EBV titer negative | |
| 29 | Famvir 250 od for 4 weeks | None | Significant clinical improvement | |
| 30 | Valacyclovir 500 mg od for 16 wks; Valacyclovir 500 mg bid for 2 wks | None | EBV panel; major decrease in symptoms; no benefit when dosage increased to bid; weaned off | Positive on Day 1; negative approx. 11 mos from Day 1 |
| 31 | Valacyclovir 500 mg od to BID for 4–6 wks | None | Transient relief of symptoms with reoccurrences; chronic, remitting with meds, EBV | Positive on Day 1; positive approx. 5 and 7 mos from Day 1 |
| 32 | Valacyclovir 500 mg od for 8 wks | Slight nausea initially - resolved in one wk | Fatigue gone; decreased antibody | Positive on Day 1 and approx. 3 mos from Day 1; negative approx. 7 mos from Day 1 |
| 33 | Valacyclovir 500 mg bid for 8 wks | None | Fatigue, sore throat gone; EBV antibody down | Positive on Day 1; negative approx. 2 mos from Day 1 |
| 34 | Valacyclovir 500 mg for 4 wks - Famciclovir 250 mg od | None | Valacyclovir lessened fatigue slightly; Famciclovir improved energy and sore throat | Positive on Day 1; no retest |
| 35 | Valacyclovir 500 mg od for 4 wks; Valacyclovir 5000BID for 12 wks; Valacyclovir 500 mg od for 4 wks | None | Significant improvement, fatigue, sore throat; lasts for several mos and reoccurs | Positive on Day 1 and approx. 3 mos from Day 1; negative approx. 7 mos from Day 1 |
| 36 | Valacyclovir 500 mg od 1or 1.5 wks; felt nauseous and HA - switched to Zovirax 200 mg od for 8 wks; tolerated this well | Headache and nausea with Valacyclovir - pt stopped - 2.5 wks later started Zovirax 200 mg od without problem | Fatigue and sore throat and swollen glands much improved - EBV antibody level unchanged; symptomatic improvement only | Positive on Day 1 and approx. 1 mo and 6 mos from Day 1 |
| 37 | Valacyclovir 500 mg bid for 8 wks | None | Fatigue, sore throat and swollen glands gone | Positive on Day 1; negative approx. 4 mos from Day 1 |
| 38 | Valacyclovir 500 mg bid for 8 wks | None | Fatigue significantly improved; EBV antibody decreased | Positive on Day 1; negative approx. 3 mos from Day 1 |
| 39 | Valacyclovir 500 mg od for 6 wks | Could not tolerate bid dose 2 mos. earlier and had stopped after a few days because of nausea; tolerated od dose without | Fatigue, sore throat gone | Positive on Day 1 and approx. 2 months from Day 1; no retest |

-continued

| PATIENT | MEDICATION | ADVERSE REACTION | RESPONSE | EBV WESTERN BLOT |
|---|---|---|---|---|
| | | problems | | |
| 40 | Valacyclovir 500 mg od for 8 wks; Valacyclovir 500 mg bid for 4 wks | None | Fatigue, sore throat, flu-like symptoms; much improved | Positive on Day 1; no retest |
| 41 | Valacyclovir 500 mg bid for 8 wks | None | Fatigue significantly improved | Positive on Day 1; negative approx. 2 months from Day 1 |
| 42 | Valacyclovir 500 bid x 12 wks | None | Fatigue; sore throat and swollen glands gone; EBV - | |
| 43 | Valacyclovir 500 od x 12 wks | None | Fatigue decreased significantly. | |
| 44 | Valacyclovir 500 bid x 12 wks | None | Fatigue was improved but in this case it is not clear whether the patient experienced relief because of the effect of Valacyclovir on EBV or not. Her EBV titer did not change. Intraoral blisters healed. Herpes Simplex ab testing for IgM component negative | |
| 45 | Valacyclovir 500 od x 4 wks | None | Fatigue, sore throat and swollen glands improved. | |
| 46 | Famciclovir 250 mg x 4 wks. | Headache | Significant decrease in fatigue | |
| 47 | Famciclovir 250 od x 2 wks | None | Decreased clinical symptoms; negative test results | |
| 48 | Famciclovir 125 mg bid x 8 wks | None | Clinical improvement | |
| 49 | Famciclovir 250 mg bid for 3 wks x 2 | None | Clinical improvement. EBV titer pending. | |
| 50 | Valacyclovir 500 bid x 4 wks; Famciclovir 250 x 4 wks; Valacyclovir 500 Tid x 2 wks; Valacyclovir 500 x 4 wks | None | 1. Awake but unable to do anything. 2. Worse 3. Better 4. Awake all day and starting to do light activity. | |
| 51 | Famciclovir 500 bid | None | Clinical improvement | |
| 52 | Valacyclovir 500 bid x 8 wks | None | Clinical improvement; Neg test | |
| 53 | Valacyclovir 500 bid x 8 weeks | None | Clinical improvement | |
| 54 | Valacyclovir 500 od x 4 wks; Valacyclovir 500 bid x 8 wks | None | Clinical improvement | |
| 55 | Valacyclovir 500 bid x 16 wks; Valacyclovir 500 od x 12 wks; Valacyclovir 500 od every 3$^{rd}$ day | None | Significant clinical improvement despite decrease | |
| 56 | Valacyclovir 500 bid x 8 wks | None | Clinical improvement | |
| 57 | Famciclovir 125 TID x 7 wks | None after initial 2 days (nervous) | Clinical improvement and negative test results | |
| 58 | Famciclovir 250 tid x 6 wks | None | Clinical improvement and negative test results | |
| 59 | Famciclovir 250 bid x 6 wks | None | Clinical improvement and negative results. | |

What is claimed is:

1. A method for treating mononucleosis in a patient which comprises administering to the patient in need thereof an effective therapeutic amount of the drug famcyclovir or a pharmaceutically acceptable salt thereof.

2. The method according to claim 1, wherein the effective therapeutic amount of the drug administered to the patient is 50 to 500 milligrams.

3. The method according to claim 1, wherein the effective therapeutic amount of the drug is administered to the patient one to two times a day.

4. The method according to claim 1, wherein the effective therapeutic amount of drug is administered to the patient for two to sixteen weeks.

* * * * *